United States Patent [19]
Didier et al.

[11] Patent Number: 6,127,555
[45] Date of Patent: Oct. 3, 2000

[54] TAXANE HYDROXY MONOACYLATION METHOD

[75] Inventors: Eric Didier, Paris; Pascal Pecquet, Ezy sur Eure, both of France

[73] Assignee: Aventis Pharma S.A., Antony, France

[21] Appl. No.: 09/214,620

[22] PCT Filed: Jul. 4, 1997

[86] PCT No.: PCT/FR97/01201

§ 371 Date: May 5, 1999

§ 102(e) Date: May 5, 1999

[87] PCT Pub. No.: WO98/01435

PCT Pub. Date: Jan. 15, 1998

[30] Foreign Application Priority Data

Jul. 9, 1996 [FR] France ................................ 96 08505

[51] Int. Cl.[7] .................................................. C07D 305/14
[52] U.S. Cl. ........................................... 549/510; 549/511
[58] Field of Search ...................... 549/510, 511

[56] References Cited

FOREIGN PATENT DOCUMENTS

| WO 94/13654 | 6/1994 | WIPO . |
| WO 94/20484 | 9/1994 | WIPO . |
| WO 95/26961 | 10/1995 | WIPO . |
| WO 95/33736 | 12/1995 | WIPO . |

OTHER PUBLICATIONS

F. Guèritte–Voegelein et al., *Chemical Studies of 10–Deacetyl Baccatin III. Hemisynthesis of Taxol Derivatives*, Tetrahedron, vol. 42, pp. 4451–4460 (1986).

J.–N. Denis et al., *A Highly Efficient, Practical Approach to Natural Taxol*, J. Am. Chem. Soc., vol. 110, pp. 5917–5919 (1988).

H.S. Mosher et al., *The Reaction of $P_2I_4$ and N,N–Dimethylformamide*, Synthetic Communications, vol. 11, pp. 733–736 (1981).

P.L. Fuchs et al., *Conversion of Amides and Lactams to Thioamides and Thiolactams Using Hexamethyldisilathiane*, J. Org. Chem., vol. 59, pp. 348–354 (1994).

A. Martinez et al., *A New Procedure for Formylation of Less Active Aromatics*, J. Chem. Soc., Chem. Commun., pp. 1571–1572 (1990).

H. Heaney et al., *Vilsmeier Formylation and Glyoxylation Reactions of Nucleophilic Aromatic Compounds Using Pyrophosphoryl Chloride*, Tetrahedron, vol. 49, pp. 4015–4034 (1993).

*Primary Examiner*—Ba K. Trinh
*Attorney, Agent, or Firm*—Finnegan, Henderson, Farabow, Garrett & Dunner, L.L.P.

[57] ABSTRACT

A process for selective monoacylation of 10-deacetylbaccatin III, or a derivative thereof in positions C-2 and C-4 possessing free hydroxyl groups in positions C-7 and C-10, using a methyleneiminium salt.

20 Claims, No Drawings

TAXANE HYDROXY MONOACYLATION METHOD

This application is a 371 of PCT/FR97/01201 dated Jul. 4, 1997.

The present invention relates to a process for the monoacylation of hydroxytaxanes. The invention relates more particularly to a process for the selective monoacylation of 10-deacetylbaccatin III or derivatives thereof.

10-Deacetylbaccatin III (10-DAB), represented by the general formula (I) in which $R_1$ represents a hydrogen atom, and baccatin III, represented by the general formula (I) in which $R_1$ represents an acetyl radical, may be extracted from yew leaves and constitute advantageous starting materials in the semi-synthesis of paclitaxel (Taxol®), docetaxel (Taxotere®) and derivatives thereof.

(I)

[Structure of formula (I) showing taxane skeleton with substituents $OR_1$, OH, HO, OCOC$_6$H$_5$, OCOCH$_3$, and numbered positions 1, 2, 4, 7, 10, 13]

However, 10-DAB is more readily accessible and is extracted from the leaves in larger amounts than baccatin III.

It is known from the work of F. Guéritte-Voegelein et al., Tetrahedron, 42, 4451–4460 (1986) that the acetylation of 10-DAB with acetic anhydride is unselective. When the reaction takes place under mild operating conditions (24 hours at 20° C.) an equimolar mixture of 7-monoacetyl and 7,10-diacetyl derivatives is formed. More vigorous conditions (48 hours at 60° C.) lead to the formation of 7,10-diacetyl and 7,10,13-triacetyl derivatives in equal amounts. At an even higher temperature (24 hours at 80° C.), the 7,10,13-triacetyl derivative is exclusively formed.

It is also known from J- N. Denis and A. E. Greene, J. Am. Chem. Soc. 110, 5917–5919 (1988) that 10-DAB can be acetylated in position 10 with acetyl chloride on condition that the hydroxyl in position 7 is selectively protected beforehand with a triethylsilyl group.

PCT application WO 95/26961 describes the preparation of baccatin III from 10-DAB in three steps: protection of the hydroxyl in position 7 by the action of a trialkylsilyl halide, acetylation of the hydroxyl in position 10 with acetic anhydride and, lastly, deprotection of the trialkylsilyl group in position 7 using trifluoroacetic acid.

Taking these results into account, it follows that any reaction allowing differentiation between the free hydroxyls in positions 7 and 10 of 10-DAB or derivatives thereof, in particular selective acylation, is of great importance in the synthesis of taxoids.

The present invention describes, for the first time, a selective monoacylation reaction of the hydroxyl in position C-10 of 10-deacetylbaccatin III or derivatives thereof in position C-2 and/or in position C-4.

It is known from W. Kantlehner, Adv. Org. Chem., vol. 9, part 2, 65–141 and 181–277 (1976) that halo-methyleneiminiums can react with alcohols to give intermediate alkoxymethyleneiminium halides which lead, after hydrolysis, to the corresponding esters with elimination of an alkylamine.

It has now been found that 10-deacetylbaccatin III or derivatives thereof in position C-2 and/or in position C-4 can be selectively monoacylated in position 10 using a methyleneiminium salt corresponding to the general formula (II):

(II)

$$\left[ \begin{array}{c} R_2 \\ X \end{array} \!\!\!\!\!\!\!\!\!\!\! \begin{array}{c} R_4 \\ N \\ R_3 \end{array} \right]^+ , Y^-$$

in which $R_2$ represents:
- a hydrogen atom,
- a straight, branched or cyclic alkyl radical containing 1 to 12 carbon atoms,
- a straight, branched or cyclic alkenyl radical containing 2 to 12 carbon atoms,
- a straight or branched alkynyl radical containing 3 to 12 carbon atoms,
- an aryl radical,
- an alkoxy, alkylamino, alkylthio, alkyloxycarbonyl, alkylaminocarbonyl or alkylthiocarbonyl group in which the alkyl part contains 1 to 12 carbon atoms, or
- a 5- or 6-membered saturated or unsaturated heterocyclic radical containing one or more hetero atoms chosen from sulfur, oxygen and nitrogen, these radicals optionally being substituted with one or more substituents chosen from:
- halogen atoms,
- alkyl or haloalkyl radicals,
- aryl radicals,
- alkylamino, piperidyl, piperazinyl, nitro or cyano groups,
- alkoxy or alkoxycarbonyl groups, the alkyl parts of the various radicals containing 1 to 12 carbon atoms, and
- 5- or 6-membered saturated or unsaturated heterocyclic radicals containing one or more hetero atoms chosen from sulfur, oxygen and nitrogen, or alternatively $R_2$ and $R_3$ or $R_2$ and $R_4$ may form, with the nitrogen atom and the methylenic carbon, a 4- to 7-membered ring, such as 2-piperidone, 2-azetidinone, 2-pyrrolidinone or caprolactam, $R_3$ and $R_4$, which are identical or different, each represent:
- a hydrogen atom,
- a straight, branched or cyclic alkyl radical containing 1 to 12 carbon atoms,
- a straight, branched or cyclic alkenyl radical containing 2 to 12 carbon atoms,
- a straight or branched alkynyl radical containing 3 to 12 carbon atoms, or
- an aryl radical, or alternatively $R_3$ and $R_4$ may form, with the nitrogen atom, an optionally substituted, saturated or unsaturated 4- to 6-membered heterocycle, X represents a halogen atom or a phosphinyloxy, phosphoranyloxy, halosulfinyloxy, halosulfonyloxy, alkylsulfonyloxy, arylsulfonyloxy, alkylaminosulfonyloxy, alkylcarbonyloxy, arylcarbonyloxy, halophosphinyloxy, halophosphoranyloxy, haloalkylsulfonyloxy or haloalkylcarbonate group, $Y^-$ represents an ion selected from halides, alkylsulfonates, arylsulfonates, alkylaminosulfonates, alkylcarboxylates, arylcarboxylates and phosphorodihalidates, or $[M(Z)_n]^-$ in which $4 \leq n \leq 6$, Z is a halogen atom and M is an element from the Periodic Table which can have an oxidation state equal to or greater than 3 and preferably between 3 and 5.

More particularly,

X represents:
- a halogen atom such as a fluorine, chlorine, bromine or iodine atom,
- a group $(Hal)_4P-O-$, $(Hal)_2PO-O-$, $(Hal)SO-O-$, $(Hal)SO_2-O-$, $R_aSO_2-O-$ or $R_aCO_2$ in which $R_a$ represents a linear, branched or cyclic alkyl radical, a haloalkyl radical, an aryl radical optionally substituted with a halogen atom or with an alkyl or nitro radical, and Hal represents a halogen atom chosen from fluorine, chlorine, bromine and iodine atoms, $Y^-$ represents:
- a halide ion such as a fluoride, chloride, bromide or iodide ion,
- a counterion such as $R_aCO_2^-$, $RSO_3^-$ or $(Hal)_2PO_2^-$, in which Hal and $R_a$ are defined as above, or
- a species such as $[M(Z)_n]^-$ in which $4 \leq n \leq 6$, Z is a halogen atom such as a fluorine or chlorine atom and M is an element from the Periodic Table which can have an oxidation state equal to or greater than 3, selected from aluminum, boron, antimony, tin and titanium.

More particularly, in the general formula (II), $R_2$ may represent a hydrogen atom or a methyl or ethyl radical or a phenyl radical.

By way of example, the following salts may be used:

N,N-dimethyl-1-trifluoromethanesulfonyloxymethylideneammonium trifluoromethanesulfonate: ($R_2=H$, $R_3=R_4=CH_3$, $X=CF_3SO_3$, $Y^-=CF_3SO_3^-$)

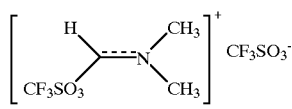

N-methyl-1-trifluoromethanesulfonyloxyethylideneammonium trifluoromethanesulfonate: ($R_2=R_3=CH_3$, $R_4=H$, $X=CH_3SO_3$, $Y^-=CF_3SO_3^-$)

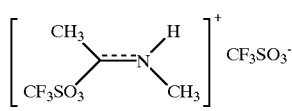

N-methyl-1-p-toluenesulfonyloxyethylideneammonium chloride: ($R_2=R_3=CH_3$, $R_4=H$, $X=p-CH_3-C_6H_4-SO_3$, $Y^-=Cl^-$) or N-methyl-1-chloroethyleneanmonium p-toluenesulfonate: ($R_2=R_3=CH_3$, $R_4=H$, $X=Cl$, $Y^{31-}=p-CH_3-C_6H_4-SO_3^{31}$)

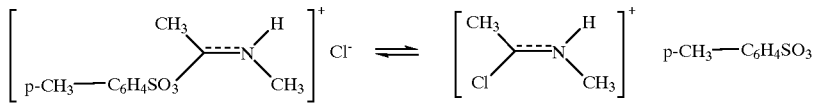

N-methyl-1-chloroethylideneammonium chloride: ($R_2=R_3=CH_3$, $R_4=H$, $X=Cl$, $Y^-=Cl^-$)

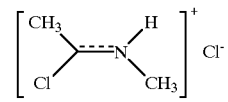

N-ethyl-1-methanesulfonyloxyethylideneammonium chloride: ($R_2=CH_3$, $R_3=C_2H_5$, $R_4=H$, $X=CH_3SO_3$, $Y^-=CH_3$) or N-ethyl-1-chloroethylideneammonium methanesulfonate: ($R_2=CH_3$, $R_3=C_2H_5$, $R_4=H$, $X=Cl$, $Y^-=CH_3SO_3^-$)

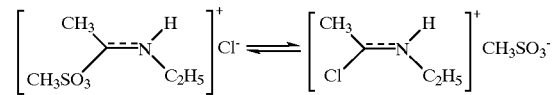

N-ethyl-1-dichlorophosinyloxyethylideneammonium chloride: ($R_2=CH_3$, $R_3=C_2H_5$, $R_4=H$, $X=O-PO-Cl_2$, $Y^-=Cl^-$) or N-ethyl-1-chloroethylideneammonium dichlorophosphoridate: ($R_2=CH_3$, $R_3=C_2H_5$, $R_4=H$, $X=Cl$, $Y^-=Cl_2PO_2^-$)

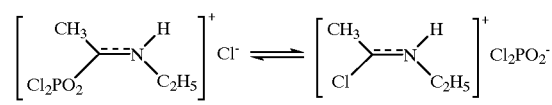

N,N-diethyl-1-p-toluenesulfonyloxyethylideneammonium p-toluenesulfonate: ($R_2=CH_3$, $R_3=R_4=C_2H_5$, $X=p-CH_3-C_6H_4-SO_3$, $Y^-=p-CH_3-C_6H_4-SO_3^-$)

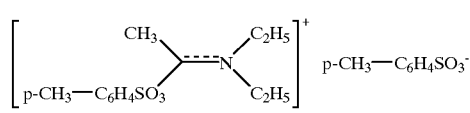

These salts may be prepared according to methods described in the literature or by processes based on these methods [see for example W. Kantlehner, Adv. Org. Chem. vol. 9, part 2, 5–64 and 65–141 (1976), R. L. N. Harris, Synthesis, 841–842 (1980), H. S. Mosher et al., Synthetic Commun., 11, 733–736 (1981), A. G. Martinez et al., J. Chem. Soc., Chem. Commun., 1571–1572 (1990), H.

Heaney et al., Tetrahedron, 49, 4015–4034 (1993), and P. L. Fuchs et al. J. Org. Chem., 59, 348–354 (1994)].

The methyleneiminium salts (II) are prepared by placing an amide of formula

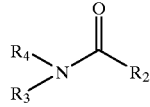

in contact with an electrophilic reactant of formula XY. They may be isolated or formed "in situ". The amide may be used both as reactant and as reaction solvent.

According to the invention, the methyleneiminium salts may react with 10-DAB and/or derivatives thereof in positions C-2 and C-4 of general formula (III):

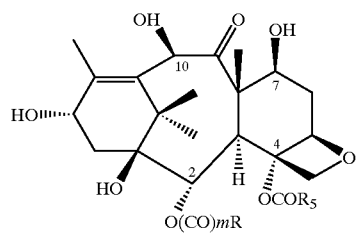

(III)

in which m may be equal to 0 or 1,

R and $R_5$, which are identical or different, represent:

a straight, branched or cyclic alkyl radical containing 1 to 8 carbon atoms, a straight, branched or cyclic alkenyl radical containing 2 to 8 carbon atoms, a straight, branched or cyclic alkynyl radical containing 3 to 8 carbon atoms, an aryl radical, or a 4- to 6-membered saturated or unsaturated heterocyclic radical containing one or more hetero atoms chosen from oxygen, nitrogen and sulfur atoms, these radicals optionally being substituted with one or more substituents chosen from:

halogen atoms such as fluorine, chlorine, bromine or iodine atoms, alkyl, hydroxyl, alkoxy, alkylthio, alkylamino, haloalkyl, haloalkoxy or haloalkylthio radicals in which the alkyl chain contains 1 to 4 carbon atoms, or 4- to 6-membered heterocyclic radicals containing one or more hetero atoms chosen from oxygen, nitrogen and sulfur atoms, which are optionally substituted, optionally substituted aryl radicals, cyano, nitro or azido groups, or carboxyl or alkoxycarbonyl groups in which the alkyl part contains 1 to 4 carbon atoms, to give a product of general formula (V):

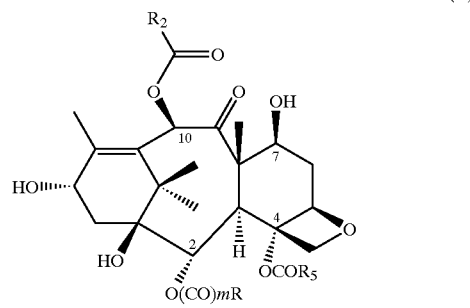

(V)

in which R, $R_2$ and R, are defined as above, via an intermediate product of general formula (IV):

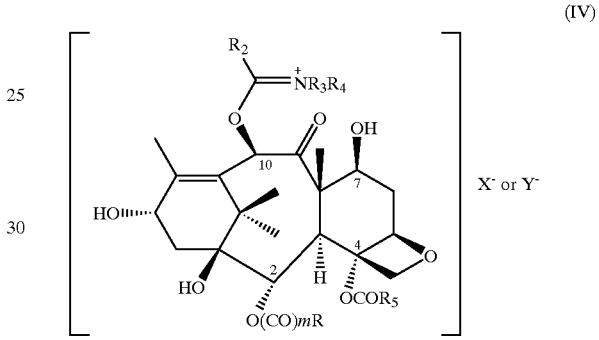

(IV)

in which m, R, $R_2$, $R_3$, $R_4$, $R_5$, $X^-$ and $Y^-$ are defined as above, which is hydrolyzed to a product of general formula (V).

The compounds of general formula (III) are defined according to the teaching of international PCT applications WO 94/20484 and WO 95/33736.

According to a better way of carrying out the invention, an excess of electrophilic reactant and/or of amide relative to the substrate of formula (III) is used.

According to a preferred mode, the excess of electrophilic reactant is less than or equal to 10 equivalents and even more preferably in the region of 5 equivalents relative to the reactant of general formula (III).

The reaction is generally carried out in an organic solvent chosen from halogenated aliphatic hydrocarbons, preferably chlorinated aliphatic hydrocarbons such as dichloromethane or 1,2-dichloroethane, aromatic hydrocarbons such as benzene, toluene or xylene, aliphatic ethers such as ethyl ether or isopropyl ether, aliphatic nitrites such as acetonitrile or aliphatic amides such as N,N-dimethylformamide, N,N-dimethylacetamide, N-ethylacetamide and N,N-diethylacetamide. It is particularly advantageous to carry out the reaction in the aliphatic amide which is used to prepare the methyleneiminium salts (II).

The process according to the invention is generally carried out at a temperature of between −78° C. and the reflux temperature of reaction mixture and preferably between −20° C. and 25° C.

It may be advantageous to carry out the process in the presence of an inorganic or organic base chosen from pyridine, trialkylamines, N-alkylmorpholines and alkali metal carbonates or bicarbonates.

The iminium salts of general formula (IV) may be hydrolyzed into a product of general formula (V) with water or using an aqueous solution of an inorganic or organic base such as sodium hydroxide, pyridine, triethylamine, sodium acetate, sodium carbonate or sodium bicarbonate.

The compounds of general formula (V) are particularly useful for the preparation of the compounds of general formula (VI):

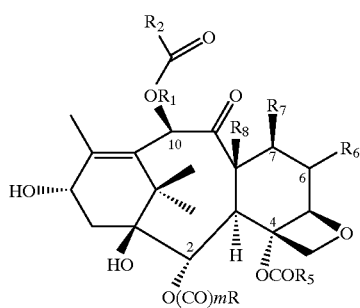

(IV)

in which, m, $R_2$ and $R_5$, are defined as above, $R_6$ represents a hydrogen atom, or f orms a bond with $R_7$ thus leading to a double bond between C-6 and C-7, $R_7$ represents:

a hydrogen atom, a halogen atom, or a hydroxyl, $OR_x$ or $O-COR_x$ group in which $R_x$ represents a hydrogen atom or a straight, branched or cyclic alkyl radical co ntaining 1 to 8 carbon atoms, a straight, branched or cyclic alkenyl radical containing 2 to 8 carbon atoms, a straight or branched alkynyl radical containing 3 to 8 carbon atoms or an aryl radical, it being understood that these radicals may optionally be substituted, or a group which increases the water-solubility, of general formula $-O-CO-A-COR_y$, in which A is an alkenyl, cycloalkenyl or aryl radical containing at least one double bond, $R_y$ represents:

a hydroxyl group, an optionally substituted alkylamino, alkylaminoalkyloxy, alkylaminoalkylthio or N,N-dialkylaminocarbonylalkoxy group containing 1 to 4 carbon atoms, and $R_8$ represents a methyl radical or forms a cyclopropyl with $R_7$.

The baccatin III of general formula (V) obtained according to the present invention is used, in particular, for the preparation of products of general formula (VI) in which $R_2$ represents a methyl radical, R, represents a hydrogen atom, $R_8$ and $R_7$ form a cyclopropyl, m is equal to 1, R represents a phenyl radical and $R_5$ represents a methyl radical, either by the action of trifluoromethanesulfonic anhydride and then an alkali metal halide (sodium chloride, sodium iodide or potassium fluoride), or with the alkali metal azide (sodium azide), or with the quaternary ammonium salt or with an alkali metal phosphate, or by the action of DAST ("diethylaminosulfur trifluoride").

It is particularly advantageous to use baccatin III or derivatives thereof of general formula (VI) obtained according to the process of the present invention, for the preparation of therapeutically active taxoids, the hydroxyl function of which in position 7 is optionally modified, of general formula (VII):

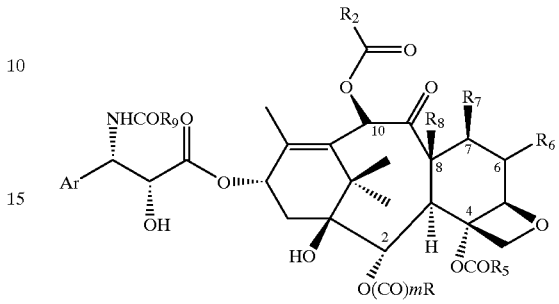

(VII)

in which m is equal to 1,

R represents a phenyl radical, $R_2$ and $R_5$ represent a methyl radical, $R_6$ represents a hydrogen atom, $R_7$ represents substituents as defined above, $R_8$ may represent a methyl radical or form with $R_7$ a cyclopropyl, and preferably, Ar represents a phenyl radical and R, represents a t-butoxy or phenyl radical.

More particularly, the baccatin III or derivatives thereof in position C-7, prepared according to the process of the present invention may be used for the synthesis of paclitaxel (Taxol®) or of the derivative of general formula (VII) in which m is equal to 1, R represents a phenyl radical, $R_2$ and $R_5$ each represent a methyl radical, $R_6$ represents a hydrogen atom, R. and $R_7$ form a cyclopropyl, Ar represents a phenyl radical and Rg represents a t-butoxy radical, as described in International application WO 94/13654.

The examples which follow illustrate the present invention.

EXAMPLE 1

Preparation of 4-acetoxy-2α-benzoyloxy-5β,20-epoxy-10β-formyloxy-1,7β,13α-trihydroxy-9-oxotax-11-ene

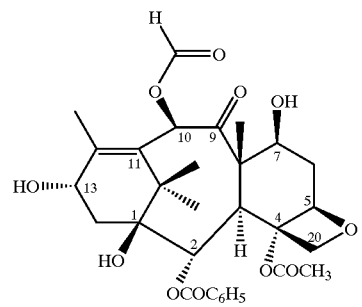

12 ml of N,N-dimethylformamide (155 mmol), 0.495 ml of pyridine (6.1 mmol) and 3 g of 97.7% 4-acetoxy-2α-benzoyloxy-5β,20-epoxy-1,7β,10β,13α-tetrahydroxy-9-oxotax-11-ene (10-DAB) (5.4 mmol) were loaded, under a nitrogen atmosphere, into a 50 ml one-necked flask fitted with a thermometer and a magnetic stirrer. After cooling to −20° C., 1.08 ml of triflic anhydride (6.4 mmol) are added over 10 minutes via a syringe. The reaction mixture is maintained at −20° C. for 10 minutes and is then hydrolyzed with 60 ml of water. After 3 hours at 0° C., the suspension is filtered and the product obtained is dried under reduced pressure at room temperature overnight. 2.87 g (4.9 mmol) of 4-acetoxy-2α-benzoyloxy-5β,20-epoxy-10β-formyloxy-1,7β,13α-trihydroxy-9-oxotax-11-ene are thus obtained, in a yield of about 90%, the purity of which compound determined by HPLC is 97% and the characteristics of which are as follows:

$^1$H NMR spectrum (400 MHz, CDCl$_3$, δ in ppm): 1.11 (s, 3H, CH$_3$); 1.13 (s, 3H, CH$_3$); 1.69 (s, 1H, OH-1); 1.71 (s, 3H, CH$_3$); 1.87 and 2.58 (2 m, 1H each, CH$_2$-6); 2.08 (s, 3H, CH$_3$); 2.18 (d, J=5.0 Hz, 1H, OH-13); 2.25 (d, J=5.0 Hz, 1H, OH-7); 2.29 (s, 3H, COOCH$_3$); 2.32 (d, J=9.0 Hz, 2H, CH$_2$-14); 3.91 (d, J=7.0 Hz, 1H, H-3); 4.16 and 4.33 (2d, J=8.5 Hz, 1H each, CH$_2$-20); 4.47 (m, 1H, H-7); 4.91 (m, 1H, H-13); 5.00 (broad d, J=10.0 Hz, 1H, H-5); 5.64 (d, J=7.0 Hz, 1H, H-2); 6.46 (s, 1H, H-10); 7.50 (t, J=7.5 Hz, 2H, meta-H in C$_6$H$_5$COO); 7.64 (t, J=7.5 Hz, 1H, para-H in C$_6$H$_5$CO); 8.13 (d, J=7.5 Hz, 2H, ortho-H in C$_6$H$_5$CO); 8;23 (s, 1H, HCO).

IR spectrum (KBr, ν in cm$^{-1}$): 3622 and 3517 (OH of H$_2$O); 3400 (OH alcohols+H$_2$O); 3061 and 3019 (CH aromatic); 2990 to 2850 (CH$_2$, CH$_3$); 1739 (C═O acetate); 1715 (C═O formate+ketone); 1704 (C═O benzoate); 1271 (O—C═O benzoate); 1250 (O—C═O acetate); 1156 (O—C═O formate); 1100 to 1000 (C—O alcohols); 977 (C—O oxetane); 719 (CH aromatic).

mass spectrum (NH3) M/Z: 590 (M+NH$_4$$^+$); 573 (M+H$^+$); 544 (M—CHO+NH$_4$$^+$); 527 (544-OH).

EXAMPLE 2

Preparation of 4,10β-diacetoxy-2α-benzoyloxy-5β,20-epoxy-1,7β,13α-trihydroxy-9-oxotax-11-ene (baccatin III)

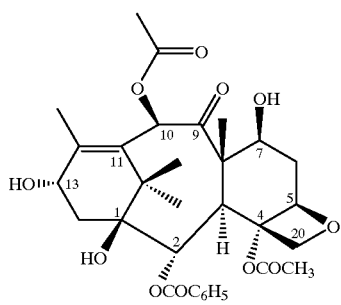

60 ml of N-ethylacetamide (627 mmol) are loaded, under nitrogen, into a 250 ml jacketed reactor fitted with a thermometer and a magnetic stirrer. After cooling to −20° C., 7.2 ml of mesyl chloride (92 mmol) are added over 15 minutes via a syringe. The solution is maintained at −20° C. for 30 minutes and then at 0° C. for about 17 hours. 10 g (10.7 mmol) of 97.5% 4-acetoxy-2α-benzoyloxy-5β,20-epoxy-1,7β,10β,13α-tetrahydroxy-9-oxotax-11-ene (10-DAB) are added to the solution, at 0° C., and the suspension is then kept stirring for 30 hours at 0° C. After transferring into a 1 liter reactor, a solution of 15 g of sodium acetate in 300 ml of water is added to the reaction mixture and the suspension obtained is then kept at room temperature for 25 hours. HPLC analysis of an aliquot of the reaction mixture makes it possible to detect less than 1% of the derivative monoacetylated in position 7 and the derivative diacetylated in positions 7 and 10. After filtration, the product is washed successively three times with 50 ml of water and dried overnight at 50° C. under reduced pressure. 9 g (14.1 mmol) of 4,10β-diacetoxy-2α-benzoyloxy-5β,20-epoxy-1,7β,13α-trihydroxy-9-oxotax-11-ene are thus obtained in a yield of 79%, the purity of which compound is 92% and the characteristics of which are as follows:

$^1$H NMR spectrum (400 MHz, CDCl$_3$, δ in ppm): 1.12 (s, 6H, CH$_3$); 1.68 (s, 4H, CH$_3$ and OH-1); 1.88 and 2.58 (2 m, 1H each, CH$_2$-6); 2.08 (s, 3H, CH$_3$); 2.27 and 2.31 (2 s, 3H each, CH$_3$CO and CH$_3$COO); 2.32 (d, J=9.0 Hz, 2H, CH$_2$-14); 3.90 (d, J=7.0 Hz, 1H, H-3); 4.17 and 4.33 (2 d, J=8.5 Hz, 1H each, CH$_2$-20); 4.48 (dd, J=11.0 Hz and 7.0 Hz, 1H, H-7); 4.91 (broad t, J=9.0 Hz, 1H, H-13); 5.00 (broad d, J=10.0 Hz, 1H, H-5); 5.64 (d, J 7.0 Hz, 1H, H-2); 6.34 (s, 1H, H-10); 7.50 (t, J=7.5 Hz, 2H, meta-H in C$_6$H$_5$COO); 7.64 (t, J=7.5 Hz, 1H, para-H in C$_6$H$_5$COO); 8.13 (d, J=7.5 Hz, 2H, ortho-H in C$_6$H$_5$COO).

IR spectrum (KBr, ν in cm$^{-1}$): 3400 (OH alcohols+H$_2$O); 3071 (CH aromatic); 2990 to 2850 (CH$_2$ and CH$_3$); 1730 (C═O acetate); 1712 (C═O formate+ketone+benzoate); 1271 (O—C═O benzoate); 1243 (O—C═O acetate); 1100 to 1000 (C—O alcohols); 982 (C—O oxetane); 710 (CH aromatic).

mass spectrum (NH$_3$) M/Z: 604 (M+NH$_4$$^+$); 587 (M+H$^+$); 544 (M—CH$_3$COOH+NH$_4$$^+$); 527 (M+CH$_3$COOH+H$^+$); 509 (M—CH$_3$COOH—H$_2$O+H$^+$).

EXAMPLE 3

3.9 g of N-methylacetamide (53 nmol) and 5 ml of 1,2-dichloroethane are loaded, under nitrogen, into a 25 ml conical flask fitted with a magnetic stirrer. After cooling to −10° C., 0.42 ml of triflic anhydride (2.5 mmol) are added and the solution is then maintained at −10° C. for 30 minutes and then at 0° C. for 1 hour. 0.5 g (about 0.9 mmol) of 4-acetoxy-2α-benzoyloxy-5β, 20-epoxy-1,7β,10β,13α-tetrahydroxy-9-oxotax-11-ene (10-DAB) is added to the solution, at 0° C. The resulting reaction mixture is kept stirring overnight at 0° C. 15 ml of aqueous 5% sodium acetate solution are then added and the mixture is then maintained at room temperature overnight. The reaction mixture is diluted by addition of 1,2-dichloroethane until dissolution is complete. The organic phase is separated out after settling has taken place and the solvent is then evaporated off under reduced pressure. In the extract obtained, about 33 mg of 4,10β-diacetoxy-2α-benzoyloxy-5β,20-epoxy-1,7β,13α-trihydroxy-9-oxotax-11-ene (baccatin III) are assayed by HPLC. The yield is in the region of 6%.

EXAMPLE 4

5 ml of acetonitrile, 3.9 g of N-methylacetamide (53 mmol) and 0.9 g of tosyl chloride (4.7 mmol) are loaded, under nitrogen and at room temperature, into a 25 ml conical flask fitted with a magnetic stirrer and the solution is then maintained at room temperature for 20 minutes. 0.5 g (about 0.9 mmol) of 4-acetoxy-2α-benzoyloxy-5β,20-epoxy-1,7β, 10β,13α-tetrahydroxy-9-oxotax-11-ene (10-DAB) is added to the solution obtained and the reaction mixture is then kept stirring for about 17 hours at room temperature. 15 ml of aqueous 5% sodium acetate solution are then added and the mixture is then kept stirring overnight at room temperature. HPLC analysis of an aliquot does not make it possible to detect any derivative monoacetylated in position 7 or derivative diacetylated in positions 7 and 10. The reaction mixture is extracted with 1,2-dichloroethane, the organic phase is separated out after settling has taken place and the solvent is evaporated off under reduced pressure. In the extract obtained, about 86 mg of 4,10β-diacetoxy-2α-benzoyloxy-5β,20-epoxy-1,7β,13α-trihydroxy-9-oxotax-11-ene (baccatin III), i.e. a yield of about 16%, are assayed by HPLC.

EXAMPLE 5

5 ml of 1,2-dichloroethane and 3.9 g of N-methylacetamide (53 mmol) are loaded, under nitrogen and at room temperature, into a 25 ml conical flask fitted with a magnetic stirrer. After cooling to 0° C., 0.4 ml of oxalyl chloride (4.6 mmol) is run in and the solution is then maintained at 0° C. for 25 minutes (formation of gas). 0.5 g (about 0.9 mmol) of 4-acetoxy-2α-benzoyloxy-5β,20-epoxy-1,7β, 10β,13α-tetrahydroxy-9-oxotax-11-ene (10-DAB) is added to the solution obtained and the reaction mixture is then kept stirring for about 19 hours at 0C. 15 ml of aqueous 5% sodium acetate solution are then added and the mixture is maintained at room temperature overnight. The reaction mixture is extracted with 1,2-dichloroethane. The organic phase is separated out after settling has taken place and the solvent is evaporated off under reduced pressure. In the extract obtained, about 212 mg of 4,10-diacetoxy-2a-benzoyloxy-5p,20 -epoxy-1,7β,13α-trihydroxy-9-oxotax-11-ene (baccatin III), i.e. a yield of about 40%., are assayed by HPLC. 1.2% of the derivative monoacetylated in position 7 is detected. The derivative diacetylated in positions 7 and 10 is not detected.

EXAMPLE 6

5 ml of 1,2-dichloroethane and 1.5 g of p-toluenesulfonic anhydride (4.5 mmol) are loaded, under nitrogen and at room temperature, into a 50 ml conical flask fitted with a magnetic stirrer. After cooling to 0° C., 4 ml of N,N-diethylacetamide (32 mmol) are added and the solution is then maintained at 0° C. for 35 minutes. 0.5 g (about 0.9 mmol) of 4-acetoxy-2α-benzoyloxy-5β,20-epoxy-1,7β,10β,13α-tetrahydroxy-9-oxotax-11-ene (10-DAB) is added to the suspension obtained. The reaction mixture is kept stirring for about 1 hour 30 minutes at 0° C. and then for 4 hours 30 minutes at room temperature. An aliquot of the solution is taken and hydrolyzed in an acetonitrile/water mixture (HPLC diluent). About 347 mg of 4,10β-diacetoxy-2α-benzoyloxy-5β,20-epoxy-1,7β,13α-trihydroxy-9-oxotax-11-ene (baccatin III), i.e. a yield of about 66%, are thus assayed by HPLC in the entire solution. No derivatives monoacetylated in position 7 or diacetylated in positions 7 and 10 are detected.

EXAMPLE 7

4 ml of N-ethylacetamide (42 mmol) and 5 ml of 1,2-dichloroethane are loaded, under nitrogen and at room temperature, into a 25 ml conical flask fitted with a magnetic stirrer. 0.42 ml of phosphorus oxychloride (4.6 mmol) is added. The solution is maintained at room temperature for 15 minutes. 0.5 g (about 0.9 mmol) of 4-acetoxy-2α-benzoyloxy-5β,20-epoxy-1,7β,10β,13α-tetrahydroxy-9-oxotax-11-ene (10-DAB) is added to the solution. The resulting reaction mixture is kept stirring for about 3 hours. An aliquot of the solution is taken and hydrolyzed in an acetonitrile/water mixture (HPLC diluent). In all of the solution, about 116 mg of 4,10β-diacetoxy-2α-benzoyloxy-5β,20-epoxy-1,7β,13β-trihydroxy-9-oxotax-11-ene (baccatin III), i.e. a yield of about 22%, are assayed by HPLC. No derivatives monoacetylated in position 7 or diacetylated in positions 7 and 10 are detected.

What is claimed is:

1. A process for the selective monoacylation of 10-deacetylbaccatin III or derivatives thereof in positions C-2 and C-4, possessing free hydroxyl groups in positions C-7 and C-10, wherein 10-deacetylbaccatin III or derivatives thereof in positions C-2 and C-4 is acylated using a methyleneiminium salt.

2. A process as claimed in claim 1, wherein the methyleneiminium salt corresponds to general formula (II):

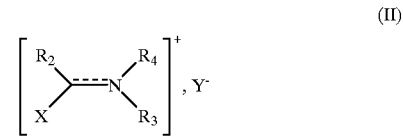

(II)

wherein $R_2$ represents:
  a hydrogen atom,
  a straight, branched, or cyclic $C_1$–C12 alkyl radical,
  a straight, branched, or cyclic $C_2$–$C_{12}$ alkenyl radical,
  a straight or branched $C_3$–$C_{12}$ alkynyl radical,
  an aryl radical,
  an alkoxy, alkylamino, alkylthio, alkyloxycarbonyl, alkylaminocarbonyl, or alkylthiocarbonyl group wherein each alkyl fragment is $C_1$–$C_{12,}$ or
  a 5- or 6-membered saturated or unsaturated heterocyclic radical containing one or more sulfur, oxygen, or nitrogen atoms,
wherein these radicals are unsubstituted or substituted with one or more substituents selected from:
  halogen atoms,
  $C_1$–$C_{12}$ alkyl or haloalkyl radicals,
  aryl radicals,
  $C_1$–$C_{12}$ alkylamino, piperidyl, piperazinyl, nitro or cyano groups,
  $C_1$–$C_{12}$ alkoxy or $C_1$–$C_{12}$ alkoxycarbonyl groups, and
  5- or 6-membered saturated or unsaturated heterocyclic radicals containing one or more sulfur, oxygen, or nitrogen atoms,
$R_3$ and $R_4$, which are identical or different, each represent:
  a hydrogen atom,
  a straight, branched, or cyclic $C_1$–$C_{12}$ alkyl radical,
  a straight, branched, or cyclic $C_2$–$C_{12}$ alkenyl radical,
  a straight or branched $C_3$–$C_{12}$ alkynyl radical, or
  an aryl radical,
or $R_3$ and $R_4$ may form, with the nitrogen atom, an unsubstituted or substituted, saturated or unsaturated 4- to 6-membered ring,
or $R_2$ and $R_3$ or $R_2$ and $R_4$ may form, with the nitrogen atom and the methylenic carbon, a 4- to 7-membered ring, X represents a halogen atom or a phosphinyloxy, phosphoranyloxy, halosulfinyloxy, halosulfonyloxy, alkylsulfonyloxy, arylsulfonyloxy, alkylaminosulfonyloxy, alkylcarbonyloxy, arylcarbonyloxy, halophosphinyloxy, halophosphoranyloxy, haloalkylsulfonyloxy, or haloalkylcarbonate group, $Y^-$ represents an ion selected from halides, alkylsulfonates, arylsulfonates, dihalidates, or $[M(Z)_n]^-$ wherein $4 \leq n \leq 6$, Z is a halogen atom, and M is an element from the Periodic Table which can have an oxidation state equal to or greater than 3.

3. A process as claimed in claim 2, wherein, in general formula (II),

X represents:
  a halogen atom,
  a group $(Hal)_4P-O-$, $(Hal)_2PO-O-$, $(Hal)SO-O-$, $(Hal)SO_2-O-$, $R_aSO_2-O$ or $R_aCO_2$ wherein $R_a$ represents a linear, branched or cyclic alkyl radical, a haloalkyl radical, an aryl radical optionally substituted with a halogen atom or with an alkyl or nitro radical, and Hal represents a fluorine, chlorine, bromine, or iodine atom, $Y^-$ represents:
  a halide ion,
  a counterion such as $R_aCO_2^-$, $R_aSO_3^-$ or $(Hal)_2PO_2^-$, wherein Hal and $R_a$ are defined as above, or
  $[M(Z)_n]^-$ wherein $4 \leq n \leq 6$, Z is a halogen atom and M is aluminum, boron, antimony, tin, or titanium, and $R_2$ represents hydrogen, a methyl or ethyl radical or a phenyl radical.

4. A process as claimed in claim 3, wherein Z is a fluorine or chlorine atom.

5. A process as claimed in claim 1, wherein the methyleneiminium salt is:

N,N-dimethyl-1-trifluoromethanesulfonyloxymethylideneammonium trifluoromethanesulfonate ($R_2$=H, $R_3$=$R_4$=$CH_3$, X=$CF_3SO_3$, $Y^-$=$CF_3SO_3^-$), N-methyl-1-trifluoromethanesulfonyloxyethylideneammonium trifluoromethanesulfonate ($R_2$=$R_3$=$CH_3$, $R_4$=H, X=$CH_3SO_3$, $Y^-$=$CF_3SO_3^-$), N-methyl-1-p-toluenesulfonyloxyethylideneammonium chloride ($R_2$=$R_3$=$CH_3$, $R_4$=H, X=p—$CH_3$—$C_6H_4$—$SO_3$, $Y^-$=$Cl^-$), N-methyl-1-chloroethylideneammonium p-toluenesulfonate ($R_2$=$R_3$=$CH_3$, $R_4$=H, X=Cl, $Y^-$=p—$CH_3$—$C_6H_4$—$SO_3^-$), N-methyl-1-chloroethylideneammonium chloride ($R_2$=$R_3$=$CH_3$, $R_4$=H, X=Cl, $Y^-$=$Cl^-$)

N-ethyl-1-methanesulfonyloxyethylideneammonium chloride ($R_2$=$CH_3$, $R_3$=$C_2H_5$, $R_4$=H, X=$CH_3SO_3$, $Y^-$=$Cl^-$), N-ethyl-1-chloroethylideneammonium methanesulfonate ($R_2$=$CH_3$, $R_3$=$C_2H_5$, $R_4$=H, X=Cl, $Y^-$=$CH_3SO_3^-$), N-ethyl-1-dichlorophosphinyloxyethylideneammonium chloride ($R_2$=$CH_3$, $R_3$=$C_2H_5$, $R_4$=H, X=O—PO—$Cl_2$, $Y^-$=$Cl^-$), N-ethyl-1-chloroethylidene-ammonium dichlorophosphoridate ($R_2$=$CH_3$, $R_3$=$C_2H_5$, $R_4$=H, X=Cl, $Y^-$=$C_2PO_2^-$), or N,N-diethyl-1-p-toluenesulfonyloxy-ethylideneammonium p-toluenesulfonate ($R_2$=$CH_3$, $R_3$=$R_4$=$C_2H_5$, X=p—$CH_3$—$C_6H_4$—$SO_3$, $Y^-$=p—$CH_3$—$C_6H_4$—$SO_3^-$).

6. A process as claimed in claim 1, wherein the 10-deacetylbaccatin III or C-2 or C-4 derivative thereof corresponds to general formula (III):

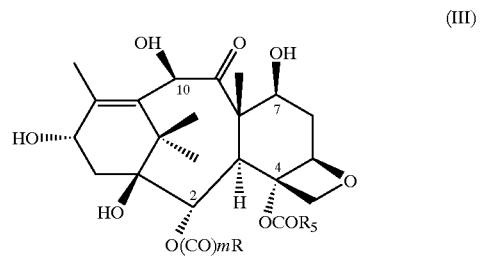

(III)

wherein:
m is equal to 0 or 1,
R and $R_5$, which are identical or different, represent:
  a straight, branched or cyclic $C_1$–$C_8$ alkyl radical,
  a straight, branched or cyclic $C_2$–$C_8$ alkenyl radical,
  a straight, branched or cyclic $C_3$–$C_8$ alkynyl radical,
  an aryl radical, or
  a 4- to 6-membered saturated or unsaturated heterocyclic radical containing one or more oxygen, nitrogen, or sulfur atoms, wherein the radicals are unsubstituted or substituted with one or more substituents selected from:
  halogen atoms,
  alkyl, hydroxyl, alkoxy, alkylthio, alkylamino, haloalkyl, haloalkoxy or haloalkylthio radicals, wherein each alkyl part is $C_1$–$C_4$,
  4- to 6-membered unsubstituted or substituted heterocyclic radicals containing one or more oxygen, nitrogen, or sulfur atoms,
  unsubstituted or substituted aryl radicals,
  cyano, nitro or azido groups, and
  $C_1$–$C_4$ carboxyl or $C_1$–$C_4$ alkoxycarbonyl groups.

7. A process as claimed in claim 6, wherein m is equal to 1, R represents a phenyl radical, and $R_5$ represents a methyl radical.

8. A process as claimed in claim 1, wherein the methyleneiminium salt is reacted with the 10-deacetylbaccatin III or C-2 or C-4 derivative thereof of general formula (III) as defined in claim 6 to obtain a product of general formula (IV):

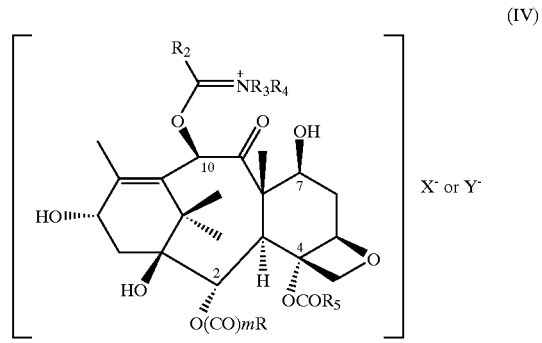

(IV)

wherein $R_2$, $R_3$, $R_4$, X, and $Y^-$ are defined as in claim 2 and m, R and $R_5$ are defined as in claim 6, said process further comprising hydrolyzing the product of general formula (IV) to provide a product of general formula (V):

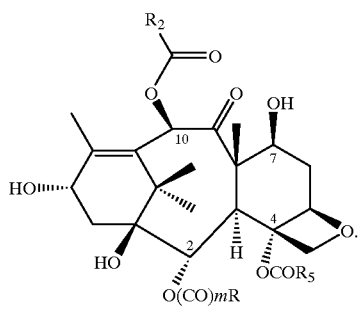

(V)

9. A process as claimed in claim 1, wherein the reaction is carried out in an organic solvent.

10. A process as claimed in claim 9, wherein the organic solvent is a halogenated organic solvent, an aromatic hydrocarbon, an aliphatic ether, an aliphatic nitrile, an aliphatic amide or a mixture thereof.

11. The process as claimed in claim 9, wherein the organic solvent is dichloromethane, 1,2-dichloroethane, benzene, toluene, xylene, ethyl ether, isopropyl ether, acetonitrile, N,N-dimethylformamide, N,N-dimethylacetamide, N-ethylacetamide, or N,N-diethylacetamide.

12. A process as claimed in claim 2, wherein the methyleneiminium salt of formula (II) is prepared by condensation of an amide of formula

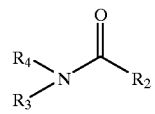

with an electrophilic reactant of formula XY, wherein:
X represents a halogen atom or a phosphinyloxy, phosphoranyloxy, halosulfinyloxy, halosulfonyloxy, alkylsulfonyloxy, arylsulfonyloxy, alkylaminosulfonyloxy, alkylcarbonyloxy, arylcarbonyloxy, halophosphinyloxy, halophosphoranyloxy, haloalkylsulfonyloxy, or haloalkylcarbonate group, and
Y⁻ represents an ion selected from halides, alkylsulfonates, arylsulfonates, alkylaminosulfonates, alkylcarboxylates, arylcarboxylates and phosphorodihalidates, or $[M(Z)_n]^-$ wherein $4 \leq n \leq 6$, Z is a halogen atom, and M is an element from the Periodic Table which can have an oxidation state equal to or greater than 3.

13. A process as claimed in claim 1, wherein the methyleneiminium salt has been previously isolated or is prepared in situ.

14. A process as claimed in claim 1, wherein the process is carried out in the presence of an electrophilic reactant in an amount of less than or equal to 10 equivalents relative to the 10-deacetylbaccatin III or C-2 or C-4 derivative thereof.

15. A process as claimed in claim 14, wherein the electrophilic reactant is present in an amount of about 5 equivalents relative to the 10-deacetylbaccatin III or C-2 or C-4 derivative thereof.

16. A process as claimed in claim 1, wherein the reaction of the methyleneiminium salt of general formula (II) with the 10-deacetylbaccatin III or C-2 or C-4 derivative thereof is carried out at a temperature of between −78° C. and the reflux temperature of the reaction mixture.

17. A process as claimed in claim 16, wherein the reaction is carried out at a temperature of from −20° C. to 25° C.

18. A process as claimed in claim 8, wherein the product of general formula (IV) is hydrolyzed with water or with an aqueous solution comprising an inorganic or organic base.

19. A process as claimed in claim 18, wherein the hydrolysis is carried out in an aqueous solution comprising sodium hydroxide, pyridine, triethylamine, sodium acetate, sodium carbonate, or sodium bicarbonate.

20. A novel baccatin III derivative of general formula (IV):

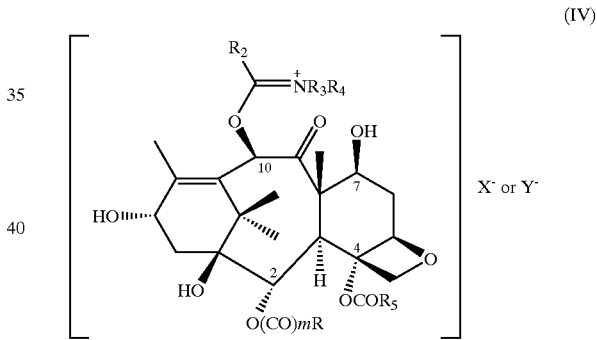

(IV)

wherein $R_2$, $R_3$, $R_4$, X, and Y⁻ are defined as in claim 2, and m, R, and $R_5$ are defined as in claim 6.

* * * * *

UNITED STATES PATENT AND TRADEMARK OFFICE
CERTIFICATE OF CORRECTION

PATENT NO. : 6,127,555
DATED : October 3, 2000
INVENTOR(S) : Eric DIDIER et al.

It is certified that error appears in the above-identified patent and that said Letters Patent is hereby corrected as shown below:

Claim 2, col. 12, line 33, "$C_1$-C12 alkyl" should read --$C_1$-$C_{12}$ alkyl--.
Claim 2, col. 13, line 9, "dihalidates," should read --alkylaminosulfonates, alkylcarboxylates, arylcarboxylates and phosphoro-dihalidates,--.
Claim 3, col. 13, line 19, "$R_aSO_2$-O" should read -- $R_aSO_2$-O- --.
Claim 5, col. 13, line 53, after "$Y^-=Cl^-$)", insert a comma.
Claim 5, col. 13, line 64, "$Y^-=C_2PO_2^-$" should read --$Y^-=Cl_2PO_2^-$--.

Signed and Sealed this

Twenty-second Day of May, 2001

*Attest:*

*Attesting Officer*

NICHOLAS P. GODICI

*Acting Director of the United States Patent and Trademark Office*